US006083186A

United States Patent [19]
Zajac

[11] Patent Number: 6,083,186
[45] Date of Patent: Jul. 4, 2000

[54] DEVICE FOR RELIEVING HEADACHE

[76] Inventor: David Zajac, 1535 Sundial Ter., El Cajon, Calif. 92021

[21] Appl. No.: 09/162,481

[22] Filed: Sep. 28, 1998

[51] Int. Cl.$^{7}$ .......... A61F 13/12
[52] U.S. Cl. .......... 602/74
[58] Field of Search .......... 602/74; 607/1, 607/46, 75, 139

[56] References Cited

U.S. PATENT DOCUMENTS

| | | | |
|---|---|---|---|
| 0,383,899 | 6/1888 | Murphy | 607/139 |
| 0,916,362 | 1/1909 | Digubonne | 607/139 |
| 0,924,596 | 6/1909 | Blushfield | 602/74 |
| 5,419,758 | 5/1995 | Vijayan | 602/74 |

FOREIGN PATENT DOCUMENTS

| | | | |
|---|---|---|---|
| 0213343 | 5/1941 | Switzerland | 607/75 |

*Primary Examiner*—William E. Kamm
*Attorney, Agent, or Firm*—Charles C. Logan, II

[57] ABSTRACT

A headband for relieving headaches and it has an elongated flat strip of plastic substrate bent into a closed loop with its ends secured to each other. An annular channel is formed on the outer surface of the flat strip and a predetermined length of electrical conductor wire is wound in a coil in the annular channel and its opposite ends terminate near each other. A short length of electrical conductor wire has its opposite ends threaded through vertically spaced apertures and onto its ends are wound the respective ends of the first electrical conductor wire. A strip of conductive aluminum foil is then secured to the outer surface of the coiled first electrical conductor wire. The ends of the second electrical conductor wire are soldered to each other and a vinyl plastic tape is wound around the outer surface of the headband.

10 Claims, 1 Drawing Sheet

DEVICE FOR RELIEVING HEADACHE

BACKGROUND OF THE INVENTION

The invention relates to headbands and more specifically to one that has been designed to relieve migraine headache pain.

Headaches are a very common disorder affecting millions of people worldwide. A common cause of headaches, concluded by present day scientific research, is dilation of the blood vessels of the head and scalp. Another common source of headaches is tension of the muscles of the head and neck. There are numerous medications on the market used to treat headaches. While medications are often effective, it is not without risk do to toxic side effects and/or the possibility of adverse reaction. Many patients therefore, opt to using drug-free types of treatments.

Over the years, various devices have been developed in order to provide headache relief. The Murphy U.S. Pat. No. 383,899, is directed to an electro-therapeutic battery having a length of insulated conducting wire wrapped in several coils and installed in the headband lining of a hat. The Dieudonne U.S. Pat. No. 910,362 is directed to a remedial electric head band that has been designed to pass around the head and act upon the forehead and temples.

The Hanke U.S. Pat. No. 1,823,686 is directed to a headband that may be moistened by water or other suitable liquid to provide a cooling effect for the band which is then placed on a person's head.

The Conrow U.S. Pat. No. 4,632,104 is directed to a device for relieving headaches by applying tension to the ear from the forward part of the skull or cranium so as to pull the ear and bring the temporal bone on which it is carried into external rotation to relieve pressure on the blood vessels and nerves carried within the temporal bone and other parts of the skull.

The Matthews U.S. Pat. No. 4,944,289 is directed to a headache relief headband having an annular strip of material having a channel defined by an outer surface and an inner surface. The plurality of pressure inducers are adapted to be inserted in this channel to apply pressure to pre-selective points on the cranium.

The Ioan U.S. Pat. No. 5,792,174 is directed to a natural headache reliever using acupuncture points. It is a cap like device having an outer membrane and an inner membrane that would be placed on the head of the wearer. The membranes meet and are attached at their margins, thus forming an inner potential space between the membranes. The inner membrane contains a plurality of immobile protrusions at a distance of between 10 mm and 20 mm apart. Direct pressure will be applied by the protrusion on different acupuncture points on the scalp and upper posterior neck. A pump is used to create the pressure by introducing air into the potential space between the inner and outer membranes.

The Vijayan U.S. Pat. No. 5,419,758 discloses a headband having a strong elastic band with a Velcro attachment at one end so that it may be applied tightly around the head to compress dilated blood vessels in order to provide relief of migraine headache pain. Additional firm rubber discs are inserted between the band and the scalp to direct more localized pressure over areas with more severe pain.

It is an object of the invention to provide a novel headband assembly that can be used for relieving headaches.

It is also an object of the invention to provide a novel headband assembly for headaches that is economical to manufacture and market.

It is another object of the invention to provide a novel headband assembly for headaches that doesn't require an electric battery for its power source.

It is an additional object of the invention to provide a novel headband assembly for headache relief that is comfortable to wear.

SUMMARY OF THE INVENTION

The novel headband assembly for relieving headaches has as its basic structure, a flat strip of plastic substrate material that is wound into a closed loop. Its free ends are secured together by a flat connection strip of plastic material that is glued to the inside surface of the respective opposite ends of the flat strip of plastic substrate material.

The outer surface of the flat strip has an annular channel or groove. A length of copper wire covered with lacquer is wound in the annular channel in a helical fashion and its opposite ends end up positioned close to each other. At this location a pair of vertically spaced apertures are formed in the flat strip of plastic substrate material. A bare copper electrical conductor wire has its opposite ends threaded through the respective apertures. The ends of the helically wound wire are cleaned free of lacquer and they are wound in loops onto the free ends of the bare copper electrical wire.

A strip of conductive aluminum foil is glued onto the outer surface of the coil of electrical wire and it extends its around entire perimeter. Covering this is a layer of non-conductive vinyl plastic tape.

DESCRIPTION OF THE PREFERRED EMBODIMENT

Figure 1:
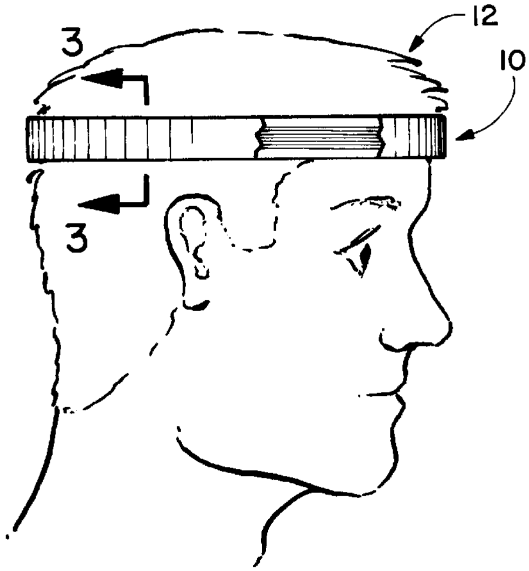
FIG. 1 is a side elevation view illustrating a person wearing the novel headband.
Figure 3:
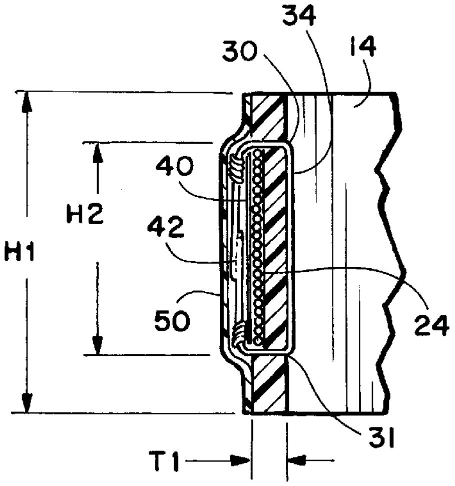
FIG. 3 is a cross sectional view taken along lines 3—3 of FIG. 1.

The novel headband assembly will now be described by referring to FIGS. 1–5 of the drawing. The headband assembly is generally designated numeral 10. The manner in which headband assembly 10 is worn is illustrated in FIG. 1 where it is shown on a person's head 12. The basic structure is a flat strip 14 of plastic substrate material bent into a closed loop. Its front end 16 and its rear end 17 are secured together by a flat connection strip 18 that has been glued to the inner surface of flat strip 14. Flat strip 14 has a height H1 that is in the range of 1.0–2.0 inches. Flat strip 14 has a thickness T1 that is in the range of 0.010–0.125 inches.

Figure 4:
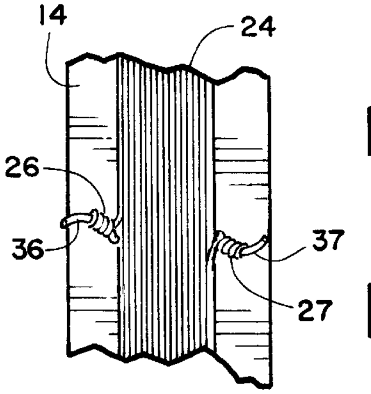
FIG. 4 is a partial side elevation view showing the manner in which the ends of the first electrical conductor wire are secured to the ends of the second electrical conductor wire.
Figure 2:
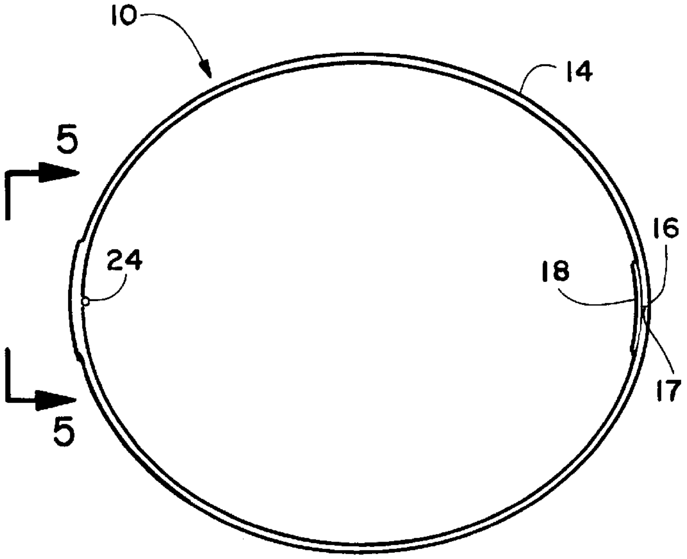
FIG. 2 is a top plan view of the novel headband.

An annular channel or groove 20 is formed in the outer surface of flat strip 14 and it has height H2 that is in the range of 0.30–1.0 inches. A predetermined length of electrical conductor wire 24 is helically wound in annular channel or groove 20. This wire is made of copper and it is covered with lacquer. The wire has a diameter of 0.015 inches. Electrical conductor wire 24 has a starting end 26 and an ending end 27. A pair of vertically spaced apertures 30 and 31 are formed in flat strip 14 adjacent the ends 26 and 27 of electrical conductor 24. An electrical conductor wire 34 has its opposite ends 36 and 37 threaded through said apertures 30 and 31 from the inside surface of flat strip 40 to its outer surface. The respective ends 26 and 27 of electrical conductor wire 24 are wound in loops on the respective ends 36 and 37 of electrical conductor wire 34. FIG. 4 shows the headband assembly at this stage.

Figure 5:
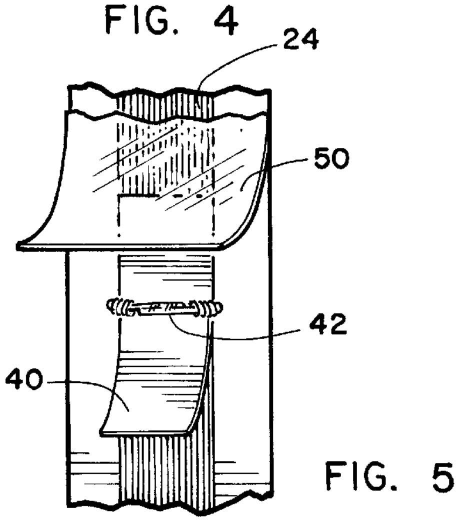
FIG. 5 is a side elevation view taken along lines 5—5 showing the manner in which the respective layers of aluminum foil and plastic tape cover the outer surface of the headband plastic substrate.

Referring to FIG. 5, the next stage in making the headband assembly is illustrated. A strip of aluminum foil 40 is glued on to the outer surface of the helically wound electrical conductor wire 24 around its entire periphery. Next the opposite ends 36 and 37 of the electrical conductor wire 34 are bent toward each other and secured together by solder 42. The final assembly step is that wrapping a layer of non-conductive vinyl plastic tape 50 around the entire perimeter of the headband. The formation of a closed loop of electrical wire 24 in combination with a strip of aluminum foil 40 glued onto the outer surface of the helically wound electrical wire 24 produces a therapeutic effect on the person wearing the headband assembly.

What is claimed is:

1. A headband for relieving headaches comprising:

an elongated flat strip of plastic substrate having a front end and a rear end; said flat strip of plastic substrate being bent into a first closed loop; means for securing said front end to said rear end to form a headband assembly; said headband assembly having an inner surface and an outer surface;

said outer surface of said headband assembly having a longitudinally extending annular channel;

a primary predetermined length of electrical conductor wire having a first end and a second end; said primary length of electrical conductor wire being wound in a coil around the outer surface of said headband assembly in said annular channel and said first and second ends terminate adjacent each other;

a pair of radially extending vertically spaced apertures in said headband assembly and they are positioned adjacent said first and second ends of said primary length of electrical conductor wire;

a secondary length of electrical conductor wire having a first end and a second end; said first and second respective ends of said secondary length of electrical wire being threaded radially outwardly through said respective pair of vertically spaced apertures from said inner surface of said headband assembly to said outer surface of said headband assembly; said first end of said primary length of electrical conductor wire being connected to said secondary length of electrical conductor wire adjacent said first end of said secondary length of electrical conductor wire; said second end of said primary length of electrical conductor wire being connected to said secondary length of electrical conductor wire adjacent said second end of said secondary length of electrical conductor wire;

means connecting said first and second ends of said secondary length of said electrical conductor wire together to form a second closed loop; and a strip of aluminum foil covering the outer surface of said coil formed by said primary length of electrical conductor wire and also inside said second closed loop formed by said secondary length of electrical conductor wire.

2. A headband for relieving headaches as recited in claim 1 wherein said means for connecting said first and second ends of said secondary length of electrical conductor wire together is a soldered connection.

3. A headband for relieving headaches as recited in claim 1 wherein said primary electrical conductor wire has a lacquer coating.

4. A headband for relieving headaches as recited in claim 1 further comprising a layer of non-conductive material covering: a) said outer surface of said strip of plastic substrate, b) said strip of aluminum foil, c) said respective first and second ends of said primary electrical conductor wire, and d) said first and second ends of said secondary electrical conductor wire.

5. A headband for relieving headaches as recited in claim 4 wherein said layer of non-conductive material is a strip of vinyl plastic tape.

6. A headband for relieving headaches as recited in claim 1 wherein said strip of aluminum foil passes all the way around the perimeter of said headband assembly.

7. A headband for relieving headaches as recited in claim 1 wherein said flat strip of plastic material has a height H1 that is in the range of 1.00–2.00 inches.

8. A headband for relieving headaches as recited in claim 1 wherein said annular channel has a height H2 that is in the range of 0.30–1.0 inches.

9. A headband for relieving headaches as recited in claim 1 wherein said flat strip of plastic material has a thickness T1 that is in the range of 0.010–0.125 inches.

10. A headband for relieving headaches as recite in claim 1 wherein said primary electrical conductor wire has a thickness in the range of 0.005–0.125 inches.

* * * * *